United States Patent [19]

Johnson et al.

[11] Patent Number: 5,098,901

[45] Date of Patent: Mar. 24, 1992

[54] IMIDAZO [1,2-B][2]BENZAZEPINE AND PYRIMIDO [1,2-B][2]BENZAZEPINE ANTIARRHYTHMIC AGENTS

[75] Inventors: Robert E. Johnson, East Greenbush; Carl A. Busacca, Ghent, both of N.Y.

[73] Assignee: Sterling Drug Inc., New York, N.Y.

[21] Appl. No.: 757,082

[22] Filed: Sep. 10, 1991

[51] Int. Cl.$^5$ .................... A61K 31/55; C07D 487/04
[52] U.S. Cl. ...................... 514/217; 540/551
[58] Field of Search .................. 540/551; 514/217

[56] References Cited

U.S. PATENT DOCUMENTS 4,354,973 10/1982 Fryer et al. .................. 260/245.7

Primary Examiner—Robert T. Bond
Attorney, Agent, or Firm—Paul Dupont

[57] ABSTRACT

Novel imidazo[1,2-b][2]benzazepines and pyrimido[1,2-b][2]benzazepines of formula I, pharmaceutical compositions containing them, methods for treating cardiac arrhythmias in mammals utilizing them, and processes for synthesizing them.

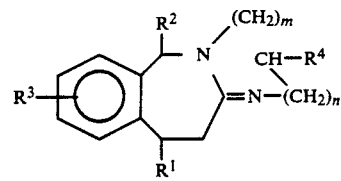

27 Claims, No Drawings

IMIDAZO [1,2-B][2]BENZAZEPINE AND PYRIMIDO [1,2-B][2]BENZAZEPINE ANTIARRHYTHMIC AGENTS

BACKGROUND OF THE INVENTION

1. Field of the Invention

The present invention relates to novel imidazo [1,2-b][2]benzazepines and pyrimido[1,2-b][2]benzazepines, to pharmaceutical compositions containing them, to methods for treating cardiac arrhythmias in mammals utilizing them, and to processes for synthesizing them.

2. Information Disclosure Statement

Applicants are unaware of any published examples of imidazo[1,2-b][2]benzazepines or pyrimido[1,2-b][2]benzazepines.

U.S. Pat. No. 4,354,973 discloses 8-chloro-6-(2-chlorophenyl)-2,4,5,6-tetrahydropyrrolo[3,4-d][2]benzazepine as a sedative and anxiolytic.

SUMMARY OF THE INVENTION

In a product aspect, the invention relates to imidazo[1,2-b][2]benzazepines and pyrimido[1,2-b][2]benzazepines of formula I

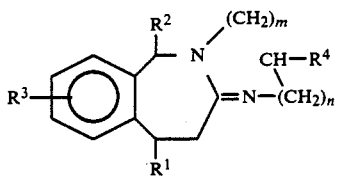

wherein $R^1$ and $R^2$ are independently hydrogen, phenyl, naphthyl, thienyl or phenyl substituted with one or two substituents chosen independently from the group consisting of lower-alkyl, lower-alkoxy and halogen;

$R^3$ is one or two substituents chosen independently from the group consisting of hydrogen, lower-alkyl, lower-alkoxy and halogen;

$R^4$ is hydrogen or phenyl m and n are each zero, one or two and the sum of m plus n is one or two.

Preferred compounds are those wherein $R^3$ and $R^4$ are hydrogen and one or the other of $R^1$ and $R^2$ is phenyl.

In a composition aspect, the invention relates to compositions for the treatment of cardiac arrhythmia which comprise compounds of formula I together with pharmaceutical carriers.

In a method aspect, the invention relates to a method for the treatment of cardiac arrhythmia which comprises administering an antiarrhythmically effective amount of a compound of formula I.

In a process aspect, the invention relates to a process for preparing compounds of formula I which comprises cyclizing a compound of formula III

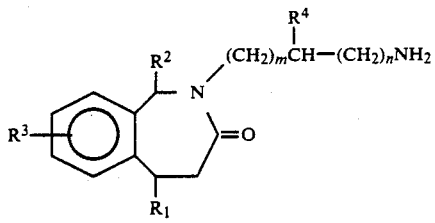

Lower-alkyl as used herein describes linear, branched, or cyclic saturated carbon chains of six or fewer carbon atoms; lower-alkoxy as used herein describes linear or branched alkoxy substituents containing six or fewer carbon atoms; halogen describes bromine, chlorine or fluorine.

In the text that follows, the substituents R are defined when initially presented and maintain that definition whenever they occur subsequently.

Detailed Description Inclusive of Preferred Embodiments

The compounds of the invention may be synthesized from 2-benzazepine-3-ones by alkylation with a protected, masked or free aminoethyl or aminopropyl halide, followed by deprotection or unmasking of the amine and dehydrative cyclization:

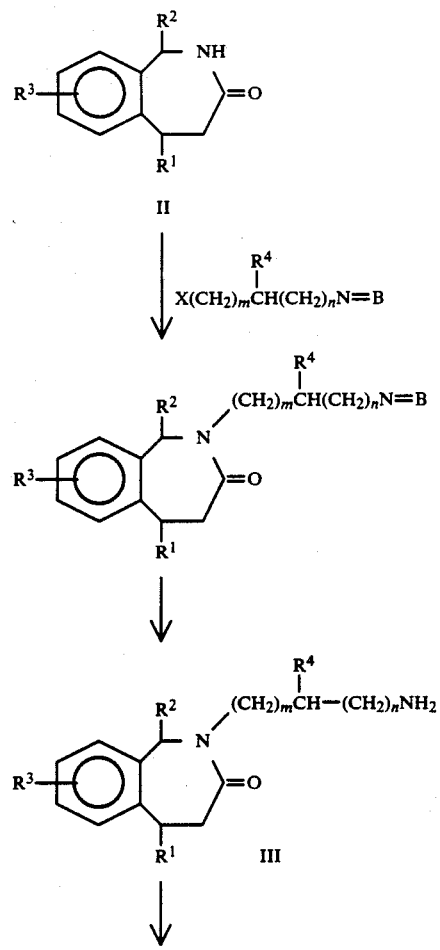

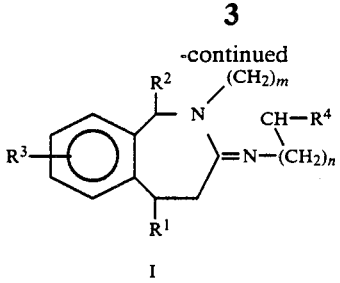

I

N=B is amino, phthalimido or dibenzylamino;
or when n is one or two, $(CH_2)_n$—N=B may be $(CH_2)_{n-1}CN$;

X is chlorine or bromine.

The benzazepinone is reacted with the halide in the presence of a base such as sodium hydride in DMF or preferably butyllithium in THF in the presence of 1,3-dimethyl-3,4,5,6- tetrahydro-2(1H)-pyrimidinone(N,N'-dimethylpropyleneurea=DMPU). When a 3-aminopropyl group is to be added (i.e. m+n =2), the phthalimide may be used; when a 2-aminoethyl group is to be added, one of the other amino-equivalents must be used because the phthalimide undergoes HX elimination rather than alkylating the benzazepine. The precursor to compounds where m+n=2 and $R^4$=H may also be made by condensing the benzazepinone with acrylonitrile in the presence of Triton B. The phthalimide is deprotected with hydrazine, the nitrile is reduced in the presence of palladium, or the benzyl protecting groups are cleaved by hydrogenolysis. The free primary amine is then dehydratively cyclized in an azeotroping solvent, optionally in the presence of a catalytic amount of an acid such as p-toluenesulfonic acid.

The benzazepinones (II) are available by syntheses known in the art. Wittekind and Lazarus [J. Het. Chem. 495-501 (1971)] describe a method for preparing benzazepinones that have electron-donating substitutents ($R^3$) in the aromatic ring. Croisier and Rodriquez (U.S. Pat. Nos. 4,080,449 and 4,080,450) describe other syntheses of benzazepinones. We have found that modifications of the method of Croisier and Rodriquez produce good yields of benzazepines having no substituents ($R^3$=H) or electron-withdrawing substituents ($R^3$=halogen):

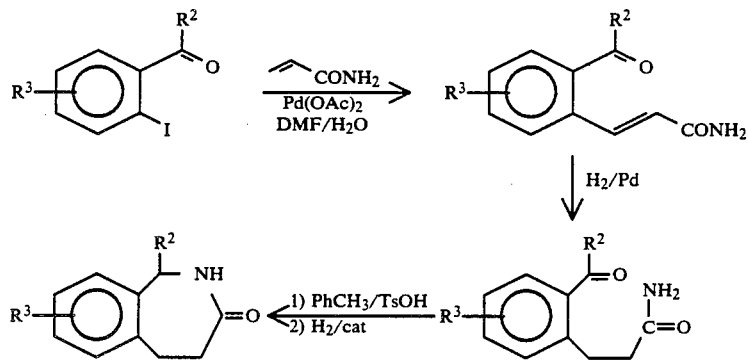

An iodobenzophenone, available by Friedel-Crafts acylation with the acid chloride of the appropriate 2-iodobenzoic acid, is condensed with acrylamide under the conditions of Zhuangyu et al. [Synth. Comm. 20, 3563-3574 (1990)]. If it is desired that $R^1$ be other than hydrogen, the resulting acrylamide may be reacted with $R^1I$ under the conditions of Zhuangyu. The acrylamide is reduced, cyclized by heating in an azeotroping solvent, optionally in the presence of an acid catalyst, and reduced again.

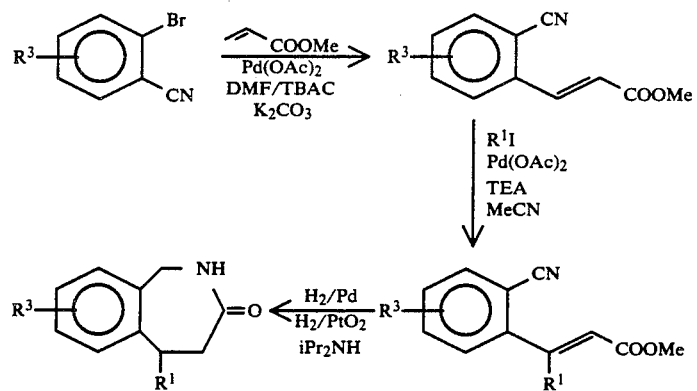

Alternatively, a 2-bromo or iodobenzonitrile may be condensed under modified Heck conditions [JACS 96, 433 (1974)] (without triphenylphosphine) with methyl acrylate and again with an iodobenzene to provide a β-aryl-2-cyanocinnamate which is then reduced with hydrogen in the presence of base, a palladium catalyst and a platinum catalyst to provide benzazepinones wherein $R^2$ is H.

It will be noted that compounds of the invention are asymmetric at the points of attachment of $R^1$, $R^2$ and $R^4$ when these groups are other than hydrogen. In some cases there may be an advantage to using one or the other enantiomer for the treatment of arrhythmia. Single enantiomers may be synthesized from chiral starting materials or the racemates may be resolved by methods well known in the art, such as chromatography on chiral media or recrystallization of diastereomeric salts.

The compounds of the invention are useful both in the free base form and the form of acid-addition salts, and both forms are within the purview of the invention. The acidaddition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. In practicing the present invention, it is convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, nuclear magnetic resonance, and mass spectroscopy. The course of the reactions and the identity and homogeneity of the products were assessed by thin layer chromatography (TLC) and high-pressure liquid chromatography (HPLC).

In the following procedures, melting points are given in degrees C and are uncorrected.

In the examples which follow, Me is methyl, Et is ethyl, Ph is phenyl, Bzl is benzyl, Bu is butyl, OAc is acetyl, THF is tetrahydrofuran, hex is hexane, IPA is isopropylamine, DMF is dimethylformamide, TMS is trimethylsilyl, PPA is polyphosphoric acid, MTBE is methyl t-butyl ether, DMPU is dimethylpropyleneurea, pTSA is p-toluenesulfonic acid, IPA is isopropylamine.

EXAMPLE 1

1-Phenyl-1,2,4,5-tetrahydro-2(3H)-benzazepine-3-one (II $R^1=R^3=H$, $R^2=Ph$)

To a mechanically stirred suspension of 248 g of 2-iodobenzoic acid (1.00 mol) in 1L of 1,2-dichloroethane at 25° was added 208 g of PCl$_5$ (1.00 mol, 1 eq.) portionwise over 45 minutes. The resulting yellow solution was stirred 3.5 h at 25°, the solvent was distilled off and the residue dissolved in 200 mL of fresh 1,2-dichloroethane, and the solvents again removed by distillation. The resultant residue was dissolved in 500 mL of benzene, cooled to −10°, and 133 g of AlCl$_3$ (1.00 mol, 1 eq.) was added in portions over 30 minutes while maintaining temperature below 10°. The reaction was then allowed to warm to 25° and maintained there for 24 h. The reaction was poured onto ice, allowed to warm to 25°, and extracted with EtOAc. The combined EtOAc layers were washed with saturated NaHCO$_3$, saturated NaCl and dried (Na$_2$SO$_4$), to furnish after solvent removal 280 g (91%) of 2-iodobenzophenone as a viscous yellow oil.

In a 100 mL flask were placed 5.00 g of 2-iodobenzophenone (16.3 mmol), 1.50 g of NaOAc (18.5 mmol, 1.13 eq.), 1.30 g of acrylamide (18.5 mmol, 1.13 eq.) 110 mg of Pd(OAc)$_2$ (0.49 mmol, ~0.03 eq.), 7.6 mL of DMF and 3.3 mL of H$_2$O in the order given. The resulting mixture was heated 24 h at 100°, cooled to 25°, poured into 75 mL of H$_2$O, and extracted well with Et$_2$O (5×75 mL). The combined Et$_2$O layers were washed with H$_2$O (2×500 mL), saturated NaCl (1×500 mL), dried (MgSO$_4$), and solvents removed in vacuo to yield 3.5 g of an oil. This oil was immediately chromatographed on SiO$_2$ eluting with EtOAc to yield 3.2 g of 2-benzoylcinnamide as a waxy solid. This solid was immediately dissolved in 100 mL of 1,4-dioxane, 0.32 g of 10% Pd/C was cautiously added, and the mixture hydrogenated at 30 psi for 6 hr. The reaction was filtered through solka floc, the solvents removed in vacuo to provide 4.8 g of an oil which was chromatographed on SiO$_2$ eluting with 1.1 hexane:EtOAc, then EtOAC to furnish 3.00 g of 2-benzoyldihydrocinnamide (72% from the benzophenone) as a yellow oil which crystallized on standing to a yellow solid, mp 72°-74°.

To a solution of 29.9 g of 2-benzoyldihydrocinnamide (118 mmol) in 1L of toluene, 3.0 g of p-TSA was added, and the mixture refluxed with a Dean-Stark water separator for 24 hr, cooled, an additional 3.0 g of p-TSA added, and the mixture refluxed for 48 hr. The resulting solution was cooled to 25°, and the solvents removed in vacuo. The residue was partitioned between saturated NaHCO$_3$ and EtOAc, the EtOAc was washed with saturated NaCl, treated with decolorizing carbon, dried (Na$_2$SO$_4$), and the solvents removed in vacuo to yield 26 g of crude dihydrobenzazepinone as an orange oil. This oil was suspended in 175 mL of absolute EtOH, 7.0 g of 10% Pd/C was cautiously added, and hydrogenation initiated at 50 psi. Hydrogen was reintroduced periodically to compensate for rapid H$_2$ takeup. After 2.5 hr, the reaction was filtered through celite, the volatiles removed in vacuo, and the residue azeotroped well with PhCH$_3$. The resultant oil was triturated with Et$_2$O to release 12.0 g of 1-phenyl-1,2,4,5-tetrahydro-2(3H)benzazepin-3-one (43%) as a white, crystalline solid, mp 166°-167°.

EXAMPLE 2

1,2,3,5,6,11-Hexahydro-11-phenylpyrimido[1,2-b][2]benzazepine (I: $R^1=R^3=R^4=H$, $R^2=Ph$, $m=n=1$)

To a suspension of 1.23 g of the benzazepinone of Example 1 (5.18 mmol) in 30 mL of benzene was added 0.14 g of NaH (5.7 mmol, ~1.1 eq.) in 2 portions, followed after 30 minutes by 0.21 g of KI (1.3 mmol, ~0.25 eq.). To this mixture was added a solution derived from 1.42 g of bromopropylamine HBr (6.48 mmol, 1.25 eq.). The free base utilized was prepared as follows: 1.42 g of amine HBr (6.48 mmol, 1.25 eq.) was dissolved in H₂O, made basic with 2N NaOH, and extracted with C₆H₆ (3×10 mL). The C₆H₆ layers were then washed with saturated NaCl, dried (K₂CO₃), and added dropwise to the aforementioned anion solution. The reaction was heated 24 hr at 40°, then an additional 0.5 g of KI was added and heated at reflux for 4 hr. The reaction was cooled to 25°, and an additional 0.14 g of NaH (5.7 mmol, ~1.1 eq.) and bromopropyl amine (from 1.42 amine HBr, 6.48 mmol, 1.25 eq.) solution were added. The mixture was further refluxed for 48 hr, cooled to 25°, and 75 mL of H₂O and 75 mL of EtOAc were added. The phases were separated, the aqueous phase was reextracted with EtOAc, and the combined organic phases were extracted with 2N HCl (2×150 mL). The combined acidic layers were then basified with conc. NH₄OH, extracted with EtOAc, and the EtOAc layers in turn washed with saturated NaCl, dried (K₂CO₃), and the solvents removed in vacuo to yield 1.32 of crude 2-(3-aminopropyl)benzazepinone as a yellow oil. This oil was immediately dissolved in 175 mL of PhCH₃, 0.87 g of p-TSA (4.6 mmol, 1 eq.) was added, and the reaction heated at reflux with a Dean-Stark water separator for 72 hr. The reaction was then cooled to 25°, an additional 0.87 g p-TSA (4.6 mmol, 1 eq.) was added and the reaction refluxed a further 48 hr. The reaction was finally cooled to 25°, the volatiles were removed in vacuo and the residue partitioned between saturated NaHCO₃ and EtOAc. The EtOAc layers were washed with saturated NaCl, dried (Na₂SO₄), and evaporated to yield 0.75 g of a waxy solid. This solid was converted to the crude HCl salt and chromatographed on neutral activity III Al₂O₃ eluting with 6% MeOH in CH₂Cl₂ to furnish 0.70 g of 1,2,3,5,6,11-hexahydro-11-phenylpyrimido[1,2-b][2]benzazepine as a white crystalline solid, mp 227°–228°.

EXAMPLE 3

10-Phenyl-1,2,4,5-tetrahydro-10H-imidazo[1,2-b][2]benzazepine (I: $R^1=R^3=R^4=H$, $R^2=Ph$, m=1, n=0)

To a solution of 1.80 g of the benzazepinone of Example 1 (7.6 mmol) in 15 mL of DMF was added 13 mg of KI (0.76 mmol, 0.01 eq.) and 200 mg of NaH (8.4 mmol, 1.1 eq.). After 1 hr at 25°, 0.58 mL of ClCH₂CN (9.2 mmol, 1.2 eq.) was added, causing a dark red solution to form. After 24 hr an additional 200 mg of NaH (8.4 mmol, 1.1 eq.) and 0.58 mL of ClCH₂CN (9.2 mmol, 1.2 eq.) were added. After a further 8 hr, 150 mL 0.5N of HCl was added, followed by 150 mL of EtOAc. The EtOAc layer was then washed with saturated NaCl (2×150 mL), dried (Na₂SO₄), and the solvents evaporated to yield 2.0 g of crude 2-cyanomethyl-1-phenyl-1,2,4,5-tetrahydro-2(3H)benzazepin-3-one as a red oil. This oil was immediately dissolved in 60 mL of glacial HOAc, 0.5% of 10% Pd/C was added, and the resulting mixture was hydrogenated for 4 hr at 50 psi. An additional 0.5 g of 10% Pd/C was added and the mixture hydrogenated a further 4 hr at 50 psi. The reaction mixture was filtered through celite, the filtrate evaporated, and the residue partitioned between 2N NaOH and EtOAc. The organic phase was washed with saturated NaCl, dried (Na₂SO₄), and evaporated to yield 0.40 g of crude 2-(2-aminoethyl compound as a yellow oil. This oil was immediately dissolved in 60 mL of PhCH₃, 50 mg of p-TSA was added, and the resulting mixture refluxed for 24hr with a Dean-Stark water separator. The reaction mixture was cooled to 25°, the volatiles were removed in vacuo, and the residue partitioned between saturated NaHCO₃ and EtOAc. The EtOAc layer was washed with saturated NaCl, dried (Na₂SO₄), and evaporated to yield 383 mg of 10-phenyl-1,2,4,5-tetrahydro-10H-imidazo[1,2-b]benzazepine free base (19%) as a viscous yellow oil. Conversion to the hydrochloride salt (EtOH/ethanolic HCl) produced as white amorphous solid, mp ~150° (dec.).

EXAMPLE 4

5-Phenyl-1,2,4,5-tetrahydro-2-(2H)-benzazepin-3-one (II: $R^1=Ph$, $R^2=R^3=H$)

In a 1L flask were placed 46.7 g of (n-Bu)₄NCl (168 mmol, 1 eq.), 35.0 g of NaHCO₃ (420 mmol, ~2.5 eq.), 30.0 g of 2-bromobenzonitrile (168 mmol, 1 eq.), 0.90 of Pd(OAc)₂ (3.6 mmol ~0.02 eq.), and 250 mL of dry DMF in the order given. To this suspension under N₂ was added 2.97 mL of methyl acrylate (333 mmol, ~2 eq.), and the reaction heated at 90° for 24 hr. The mixture was diluted with H₂O (300 mL), and extracted with Et₂O (3×500 mL). The combined ethereal phases were washed with H₂O (2×1L), saturated NaCl (1×1L), dried (Na₂SO₄) and the solvents removed to yield 35 g of a grey solid. This solid was recrystallized from THF to ultimately yield 30.5 g (97%) of methyl 2-cyanocinnamate as a yellow solid, mp 92°–93°.

In a 350mL steel bomb were placed 25.0 g of the cinnamate (134 mmol, 1 eq.), 15.0 mL of iodobenzene (134 mmol, 1 eq), 18.7 mL triethylamine 134 mmol, 1 eq.), 0.30 g of Pd (OAc)₂ (1.34 mmol, 0.01 eq.) and 80 mL of CH₃CN in the order given. The mixture was stirred until homogeneous, the head space was displaced with N₂ and the bomb sealed. After stirring and heating at 100° for 48 hr, the bomb was cooled, opened and the contents added to 400 mL of 1N HCl. The resulting mixture was extracted with CH₂Cl₂ (3×300 mL), the CH₂Cl₂ layers washed with saturated NaHCO₃, treated with decolorizing carbon, dried (MgSO₄) and the solvents removed to yield a dark red oil. This material was immediately chromatographed on SiO₂ eluting with hexane (to remove biphenyl) followed by 4:1 hexane:ethyl acetate. Concentration of the active fractions provided 30.0 g of crude phenylcinnamate as an amorphous solid. This solid was recrystallized from Et₂O/EtOH to furnish, after drying, 22.7 g (67%) of methyl 2-cyano-β-phenylcinnamate as a colorless solid, mp 114°–116°.

The phenylcinnamate (0.50 g, 1.80 mmol) was dissolved in 25 mL of absolute EtOH and 5 mL of diisopropylamine. To this was added 250 mg of 10% Pd/C and 125 mg of PtO₂ and the suspension hydrogenated for 4 hr at 50°. The mixture was filtered and the solvents removed in vacuo to provide an oil which was dissolved in PhCH₃ (200 mL) and heated at reflux for 30 minutes. Toluene removal in vacuo provided a crude solid which on trituration with Et₂O provided 0.32 g (75%) of 5- phenyl-1,2,4,5-tetrahydro-2(3H)-benzazepin-3-one as a colorless crystalline solid, mp 180°–181°.

EXAMPLE 5

5-Phenyl-1,2,4,5-tetrahydro-10H-imidazo[1,2-b][2]benzazepine (I: $R^1=Ph$, $R^2=R^3=R^4=H$, m=1, n=0)

A suspension of 1.80 g of the benzazepinone of Example 4, (7.59 mmol) in 30 mL of THF was cooled to 0° under $N_2$ and then treated dropwise with 3.36 mL of 2.5 M n-BuLi (8.40 mmol, 1.1 eq.) to produce a clear, pale yellow solution. After 15 minutes at 0°, 15 mL of DMPU was added dropwise. To this was added a solution of the free base prepared from 2.70 of N,N-dibenzyl chloroethylamine hydrochloride (9.11 mmol, 1.2 eq.). The resulting reaction mixture was allowed to warm to 25°, 0.32 g of dry KI (1.90 mmol, 0.25 eq.) was added, and heated at gentle reflux for 48 hr. Saturated $NH_4Cl$ (4 mL) was then added, and the THF removed in vacuo. The residue was partitioned between 2N NaOH and $Et_2O$, and the aqueous portion reextracted with $Et_2O$. The combined $Et_2O$ layers were washed with $H_2O$ (2×500 mL), dried ($MgSO_4$), and the solvents removed to yield 4.10 g of a yellow oil. The oil was chromatographed on $SiO_2$ eluting with 2:1 hexane:ethyl acetate, then $CH_2Cl_2$ to provide 1.80 (51%) of 2-[2-[bis(-phenylmethyl)amino]ethyl]-5-phenyl-1,2,4,5-tetrahydro- 2(3H)benzazepin-3-one as a viscous yellow oil.

To a solution of 1.40 g of dibenzylaminolactam (3.04 mmol) in 50 mL of MeOH was added 0.70 g of 10% Pd/C. The resulting suspension was heated to reflux and 0.99 g of $NH_4HCO_2$ (15.6 mmol, ~5 eq.) was added neat, at once. After 2 hr, the reaction mixture was cooled, filtered through solka floc and the pad washed well with $CHCl_3$. The filtrate was evaporated to provide an oil which was partitioned between 2N NaOH and $Et_2O$. The aqueous phase was reextracted with $Et_2O$, the combined $Et_2O$ phases dried ($MgSO_4$), and the solvents removed to yield 0.80 g crude free amine as a yellow oil. This oil was immediately dissolved in 250 mL of xylenes and heated to reflux with a Dean-Stark water separator for 48 hr. The solvents were then removed in vacuo to yield a semi-solid which was converted to the crude HCl salt (THF/$Et_2O$/HCl) and chromatographed on neutral activity grade III $Al_2O_3$ eluting with 6% MeOH in $CH_2Cl_2$. Recrystallization of the solid thus obtained from $Et_2O$/MeOH provided 0.55 g of 5-phenyl-1,2,4,5- tetrahydro-10H-imidazo[1,2-b][2]benzazepine as its HCl salt (60% from the dibenzylamine) as a white solid, mp 200°-201°.

EXAMPLE 6

1,2,3,5,6,11-Hexahydro-7-phenylpyrimido[1,2-b][2]benzazepine (I: $R^1$=Ph, $R^2$=$R^3$=$R^4$=H, m=n=1)

A suspension of 1.49 g of the benzazepinone of Example 4 in 25 ml THF was cooled to 0° under $N_2$ and treated dropwise with 2.78 mL of 2.5 M n-BuLi (6.95 mmol, 1.1 eq.) to produce a clear, pale yellow solution. After 15 minutes, 17 mL of DMPU was added dropwise, followed after an additional 15 minutes by 1.85 of 3-bromopropylphthalimide (6.95 mmol, 1.1 eq.) in 10 mL of THF, dropwise. The reaction mixture was allowed to warm to 25° and maintained there for 24 hr. Saturated $NH_4Cl$ (3 mL) was added, followed by 20 mL of $H_2O$. The resulting suspension was filtered, solids were washed well with $H_2O$ and dried in vacuum oven. The filtrate was extracted with $Et_2O$ (3×200 mL), and the combined $Et_2O$ phases washed with $H_2O$ (2×200 mL), saturated NaCl (1×300 mL), L dried ($MgSO_4$), and the solvents evaporated to yield 1.3 g of a semi-solid. This material was triturated with $Et_2O$, filtered and dried in a vacuum oven. Combined yield of both solids 2.00 g (75%) of 2-(3-phthalimidopropyl)-5-phenyl-1,2,4,5-tetrahydro-2(3H)-benzazepin-3-one as a white solid, mp 172°-173°.

A suspension of 0.21 g of phthalimido lactam (0.50 mmol) in 6 mL of absolute EtOH was treated with 52 μl of $H_2NNH_2.H_2O$ (1.09 mmol, 2.2 eq.). The resulting suspension was heated to reflux for 30 minutes. An additional 52 μl of $H_2NNH_2.H_2O$ was added, and the reaction refluxed for 1 hr. The reaction was cooled to 25°, filtered, and the solid washed well with EtOH. The filtrates were then evaporated to yield 0.22 g of crude 2-(3-aminopropyl)benzazepinone as a waxy yellow solid. This solid was immediately dissolved in 50 mL of xylenes and heated at reflux with a Dean-Stark water separator for 24 hr. The solvents were removed in vacuo to provide an oil which was chromatographed on $SiO_2$ eluting with 5:1 MTBE:IPA to provide 120 mg (88%) of 1,2,3,5,6,11- hexahydro-6-phenylpyrimido[1,2-b][2]benzazepine free base as a crystalline yellow solid, mp 138°-141°. This solid was dissolved in $Et_2O$/MeOH and converted to the HCl salt with ethereal HCl. Recrystallization of the salt from $Et_2O$/MeOH provided 110 mg of the hydrochloride as a white solid, mp 248°-249°.

EXAMPLE 7

7-Chloro-1-phenyl-1,2,4,5-tetrahydro-2(3H)-benzazepin-3-one (II: $R^1$=H, $R^2$=Ph, $R^3$=Cl)

A solution of 1.47 g of $PCl_5$ (7.08 mmol, 1 eq.) in 35 mL of 1,2-dichloroethane was cooled to 0° under $N_2$, then 2.00 g of 2-iodo-4-chlorobenzoic acid (7.08 mmol), 1 eq.) was added neat, at once. The bath was removed, the reaction allowed to warm to 25° and maintained there for 3 hr. The volatiles were removed in vacuo, the residue dissolved in 35 mL of fresh 1,2-chloroethane and again evaporated. The residual oil was dissolved in 70 mL of benzene, cooled to 0° and treated with 0.94g of $AlCl_3$ (7.08 mmol, 1 eq.). After 1 hr at 0°, the reaction was allowed to warm to 25° and maintained there overnight. The mixture was poured onto 200 mL of ice, warmed and extracted with $Et_2O$ (3×100 mL). The combined $Et_2O$ layers were washed with saturated $NaHCO_3$ (2×200 mL), saturated NaCl (1×300 mL), dried ($MgSO_4$), and the solvents removed in vacuo to yield 2.00 g (82%) of 4-chloro-2-iodobenzophenone as a yellow oil.

In a 100 mL steel bomb were placed 2.00 g of the benzophenone (5.84 mmol), 0.54 g of NaOAc (6.6 mmol ~1.13 eq.), 0.465 g of acrylamide (6.6 mmol, ~1.13 eq.), 39 mg of Pd(OAc)$_2$ (0.18 mmol, ~0.03 eq.), 5 mL of DMF and 2.2 mL of $H_2O$ in the order given. The bomb was sealed and heated at 125° for 16 hr, cooled to 0°, opened and diluted with about 50 mL of $H_2O$. This solution was extracted with $Et_2O$ (4×100 mL), and the combined $Et_2O$ layers washed with $H_2O$ (2×200 mL), saturated NaCl (1×200 mL), dried ($MgSO_4$), and the solvents removed to yield 1.4 g crude 2-benzoyl-5-chlorocinnamide as an amorphous solid which was immediately dissolved in 50 mL of 1,4-dioxane, 150 mg of 10% Pd/C was cautiously added, and hydrogenated for 3 hr at 50 psi. An additional 300 mg of 10% Pd/C was added and the mixture hydrogenated for a further 2 hr at 50 psi. The reaction mixture was filtered and the solvents removed in vacuo to yield 1.5 g of an oil which was immediately chromatographed on $SiO_2$ eluting with 2:1 hexane:EtOAc, followed by EtOAc. In this fashion, 1.24 g pure 2-benzoyl-5-chlorodihydrocinnamide was obtained as a viscous yellow oil.

To a solution of 470 mg of ketoamide (1.63 mmol) in 20 mL of PhCH$_3$ was added 20 mg of p-TSA and the reaction heated to reflux with a Dean-Stark water separator. After 24 hr, an additional 20 mg p-TSA was added and the mixture again heated for 24 hr. The solvents were then removed in vacuo and the residue partitioned between saturated NaHCO$_3$ and EtOAc. The organic layer was dried (Na$_2$SO$_4$) and the solvents removed to yield 0.42 g of crude dihydrobenzazepinone as a yellow oil. This oil was immediately dissolved in 50 mL of absolute EtOH, 150 mg of 10% Pd/C was added, and the mixture hydrogenated for 2.5 hr at 50 psi. The reaction mixture was filtered and the solvents removed in vacuo to provide a yellow oil. Trituration with 2:1 EtOAc:hexane caused formation of a white crystalline precipitate, 220 mg (50% from ketoamide) of 7- chloro-1-phenyl-1,2,4,5-tetrahydro-2(3H)-benzazepin-3-one, mp 204°–205°.

EXAMPLE 8

7-Chloro-1,10-diphenyl-1,2,4,5-tetrahydro-10H-imidazo[1,2-b][2]benzazepine (I: $R^1$=H, $R^2$=$R^4$=Ph, $R^3$=Cl, m=0, n=1)

By a procedure analogous to that of Example 2, it is contemplated that 7-chloro-1,10-diphenyl-1,2,4,5-tetrahydro-10H-imidazo[1,2-b][2]benzazepine may be synthesized from 7- chloro-1-phenyl-1,2,4,5-tetrahydro-2(3H)-benzazepin-3-one of Example 7 and β-chlorophenethylamine (see Barnett et al. *J. Chem. Soc.*, 1944. 94–96).

The compounds of this invention having formula I have antiarrhythmic activity as shown by the results of standard pharmacological tests carried out on representative examples as described below.

Antiarrhythmic activity was demonstrated by a procedure, which is a modification of standard programmed electrophysiological techniques utilized in large animals and in clinical studies in humans. Male Duncan-Hartley guinea pigs (600–800 grams) were anesthetized with sodium pentobarbital (30 mg/kg, i.p.) and artificially ventilated with a Harvard small-animal respirator. A left thoracotomy was performed and a fluid-filled catheter and transducer (Millar Micro-tip, Model 4F, Millar Inst. Inc., Houston, Texas) were inserted through the anterior wall of the left ventricle to monitor left ventricular pressure (LVP). The first derivative of the LVP (dP/dt) was obtained from a Grass differentiator (Model 7P20B) and used as an index of contractile function. A lead II EKG along with LVP and dP/dt were continuously recorded on a Grass polygraph (Model 7B). Rate pressure product (RPP), an index of cardiac work, was calculated using peak systolic LVP and heart rate (HR).

Effective refractory periods (ERP) were evaluated during left ventricular pacing. Grass subcutaneous electrodes were implanted as bipolar ventricular electrodes to deliver stimuli from a Bloom DTU-2 stimulator (Bloom Electronics, Inc., Reading, Pennsylvania) and stimulus isolation unit. Hearts were stimulated at the slowest frequency allowing consistent pacing (S1, 240–300 bpm) using 2 ms pulses at twice diastolic threshold. Threshold was determined by increasing the stimulation voltage until a 1:1 capture of the ventricular response with the stimulus was observed. A train of 8 normal pulses was delivered followed by a premature (S2) pulse. The interval between the last S1 and the premature S2 pulse was reduced in 10-ms increments until a ventricular response was not initiated. The longest S1-S2 interval that failed to produce a ventricular response was defined as the ERP. Pacing stimuli and the EKG were displayed at a sampling frequency of 92 Hz on an Apple IIe microcomputer using a two-channel 8-bit A/D converter (R.C. Electronics, Compu-Scope APL-D2, Santa Barbara, California).

Baseline hemodynamic function was evaluated followed by ventricular pacing to determine ERP. Pacing was discontinued prior to drug administration and resumed at set intervals during the protocol to evaluate ERP. Test compounds were administered (1 mL/kg) via the left ventricular catheter over a 15-second interval for doses less than 10 mg/kg. Higher doses (>10 mg/kg) were slowly infused over a 1-minute interval. Doses were cumulatively increased every 15 minutes until a maximally tolerated dose which reduced dP/dt by 50% was noted. Ten minutes after each dose, hemodynamics and ERP were reevaluated.

Data were analyzed using an analysis of variance for repeated measures of raw data and are expressed as means. An effective dose to increase ERP by a minimum of 20 msecs (ED$_{20}$), which was consistently a statistically significant increase, was derived for each animal from a linear regression of the data and expressed as a mean for the treated population. Biological significance was established at a probability of error less than 0.05. The results are presented in Table A.

TABLE A

| Example | ED$_{20}$ mg/kg |
|---------|-----------------|
| 2 | 2.0 |
| 3 | 0.5 |
| 5 | 0.3 |
| 6 | 0.1 |

The pharmaceutical compositions of the present invention include one or more of the compounds of this invention formulated into compositions together with one or more nontoxic physiologically acceptable carriers, adjuvants or vehicles which are collectively referred to herein as carriers, for parenteral injection, for oral administration in solid or liquid form, for rectal or topical administration, and the like.

The compositions can be administered to humans and animals either orally, rectally, or parenterally (intravenously, intramuscularly or subcutaneously).

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethyleneglycol, glycerol and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispersing agents. Prevention of the action of microorganisms can be ensured by various antibacterial and antifungal agents, for example, parabens, chlorobutanol, phenol, sorbic acid, and the like. It may also be desirable to include isotonic agents for example sugars, sodium chloride and the like. Prolonged absorption of the injectable pharmaceutical form can be brought about by the use of agents delaying absorption; for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

We claim:
1. A compound of formula

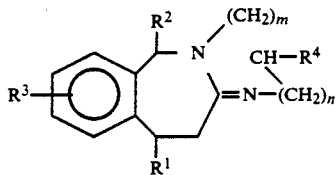

or an acid-addition salt thereof wherein
$R^1$ and $R^2$ are independently hydrogen, phenyl, naphthyl, thienyl or phenyl substituted with one or two substituents chosen independently from the group consisting of lower-alkyl, lower-alkoxy and halogen;
$R^3$ is one or two substituents chosen independently from the group consisting of hydrogen, lower-alkyl, lower-alkoxy and halogen;
$R^4$ is hydrogen or phenyl
m and n are each zero, one or two and the sum of m plus n is one or two.

2. A compound according to claim 1 wherein m plus n is one.

3. A compound according to claim 2 wherein $R^1$ is hydrogen.

4. 10-Phenyl-1,2,4,5-tetrahydro-10H-imidazo[1,2-b][2]benzazepine according to claim 3.

5. A compound according to claim 2 wherein $R^2$ is hydrogen.

6. 5-Phenyl-1,2,4,5-tetrahydro-10H-imidazo[1,2-b][2]benzazepine according to claim 5.

7. A compound according to claim 1 wherein m plus n is two.

8. A compound according to claim 7 wherein $R^1$ is hydrogen.

9. 1,2,3,5,6,11-Hexahydro-11-phenylpyrimido[1,2-b][2]benzazepine according to claim 8.

10. A compound according to claim 7 wherein $R^2$ is hydrogen.

11. 1,2,3,5,6,11-Hexahydro-6-phenylpyrimido[1,2-b][2]benzazepine according to claim 10.

12. A composition for the treatment of cardiac arrhythmia in a patient in need of such treatment which comprises a pharmaceutical carrier and an antiarrhythmically effective amount of a compound according to claim 1.

13. A composition for the treatment of cardiac arrhythmia in a patient in need of such treatment which comprises a pharmaceutical carrier and an antiarrhythmically effective amount of a compound according to claim 4.

14. A composition for the treatment of cardiac arrhythmia in a patient in need of such treatment which comprises a pharmaceutical carrier and an antiarrhythmically effective amount of a compound according to claim 6.

15. A composition for the treatment of cardiac arrhythmia in a patient in need of such treatment which comprises a pharmaceutical carrier and an antiarrhythmically effective amount of a compound according to claim 9.

16. A composition for the treatment of cardiac arrhythmia in a patient in need of such treatment which comprises a pharmaceutical carrier and an antiarrhythmically effective amount of a compound according to claim 11.

17. A method for the treatment of cardiac arrhythmia in a patient in need of such treatment which comprises the administration of an antiarrhythmically effective amount of a compound according to claim 1.

18. A method for the treatment of cardiac arrhythmia in a patient in need of such treatment which comprises the administration of an antiarrhythmically effective amount of a compound according to claim 4.

19. A method for the treatment of cardiac arrhythmia in a patient in need of such treatment which comprises the administration of an antiarrhythmically effective amount of a compound according to claim 6.

20. A method for the treatment of cardiac arrhythmia in a patient in need of such treatment which comprises the administration of an antiarrhythmically effective amount of a compound according to claim 9.

21. A method for the treatment of cardiac arrhythmia in a patient in need of such treatment which comprises the administration of an antiarrhythmically effective amount of a compound according to claim 11.

22. A process for the preparation of a compound according to claim 1 which comprises cyclizing a compound of formula

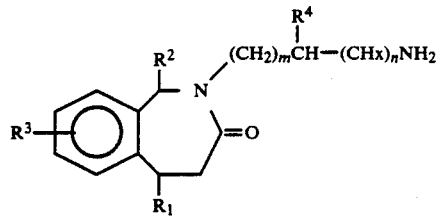

23. A method for the treatment of cardiac arrhythmia in a patient in need of such treatment which comprises the administration of a composition according to claim 12.

24. A method for the treatment of cardiac arrhythmia in a patient in need of such treatment which comprises the administration of a composition according to claim 13.

25. A method for the treatment of cardiac arrhythmia in a patient in need of such treatment which comprises the administration of a composition according to claim 14.

26. A method for the treatment of cardiac arrhythmia in a patient in need of such treatment which comprises the administration of a composition according to claim 15.

27. A method for the treatment of cardiac arrhythmia in a patient in need of such treatment which comprises the administration of a composition according to claim 16.

* * * * *